United States Patent [19]

Kolman et al.

[11] 4,027,971

[45] June 7, 1977

[54] METHOD OF SIMULTANEOUSLY COUNTING BLOOD CELLS

[76] Inventors: Philip Kolman, 26 Glen Brook Road, Monsey, N.Y. 10942; Maurice J. Dunn, 90 Charles St., Lindenhurst, N.Y. 11757; David Tiersten, 57 Curtiss Place, Maplewood, N.J. 07040

[22] Filed: Oct. 30, 1975

[21] Appl. No.: 627,187

Related U.S. Application Data

[63] Continuation of Ser. No. 321,755, Jan. 8, 1973, abandoned.

[52] U.S. Cl. .............................. 356/36; 23/230 B; 250/222 PC; 356/39; 356/201; 356/208
[51] Int. Cl.² ...................................... G01N 33/16
[58] Field of Search ............... 23/230 B, 258.5; 250/222 PC; 356/36, 39, 73, 102, 184, 186, 188, 201, 208

[56] References Cited

UNITED STATES PATENTS

| 2,875,666 | 3/1959 | Parker et al. | 250/222 PC |
| 3,523,733 | 8/1970 | Kling et al. | 356/102 X |
| 3,580,683 | 5/1971 | Schulkind | 356/186 X |
| 3,819,276 | 6/1974 | Keiss et al. | 356/201 X |

OTHER PUBLICATIONS

Strobel, H. A., *Chemical Instrumentation*, Addison–Wesley Publishing Co. Inc., Reading, Mass. 1960, pp. 150–159.

*Primary Examiner*—John K. Corbin
*Assistant Examiner*—F. L. Evans
*Attorney, Agent, or Firm*—Hopgood, Calimafde, Kalil, Blaustein & Lieberman

[57] ABSTRACT

An analytical apparatus includes means for simultaneously counting the quantity of blood cells, either erythrocytes or leucocytes, suspended in a predetermined quantity of fluid comprising a blood fraction as well as for determining the quantity of a chemical constituent in a given blood volume by the use of filter photometry. White light which is directly transmitted through a predetermined volume of such fluid containing the suspended blood cells whose overall quantity is to be simultaneously counted is filtered through a light filter having an optical wavelength selected to substantially minimize any interference from any spurious chemical substances contained within the blood fraction due to absorption of the initial light by the spurious substance while passing light of the selected optical wavelength which has not been absorbed by the blood cells.

5 Claims, 7 Drawing Figures

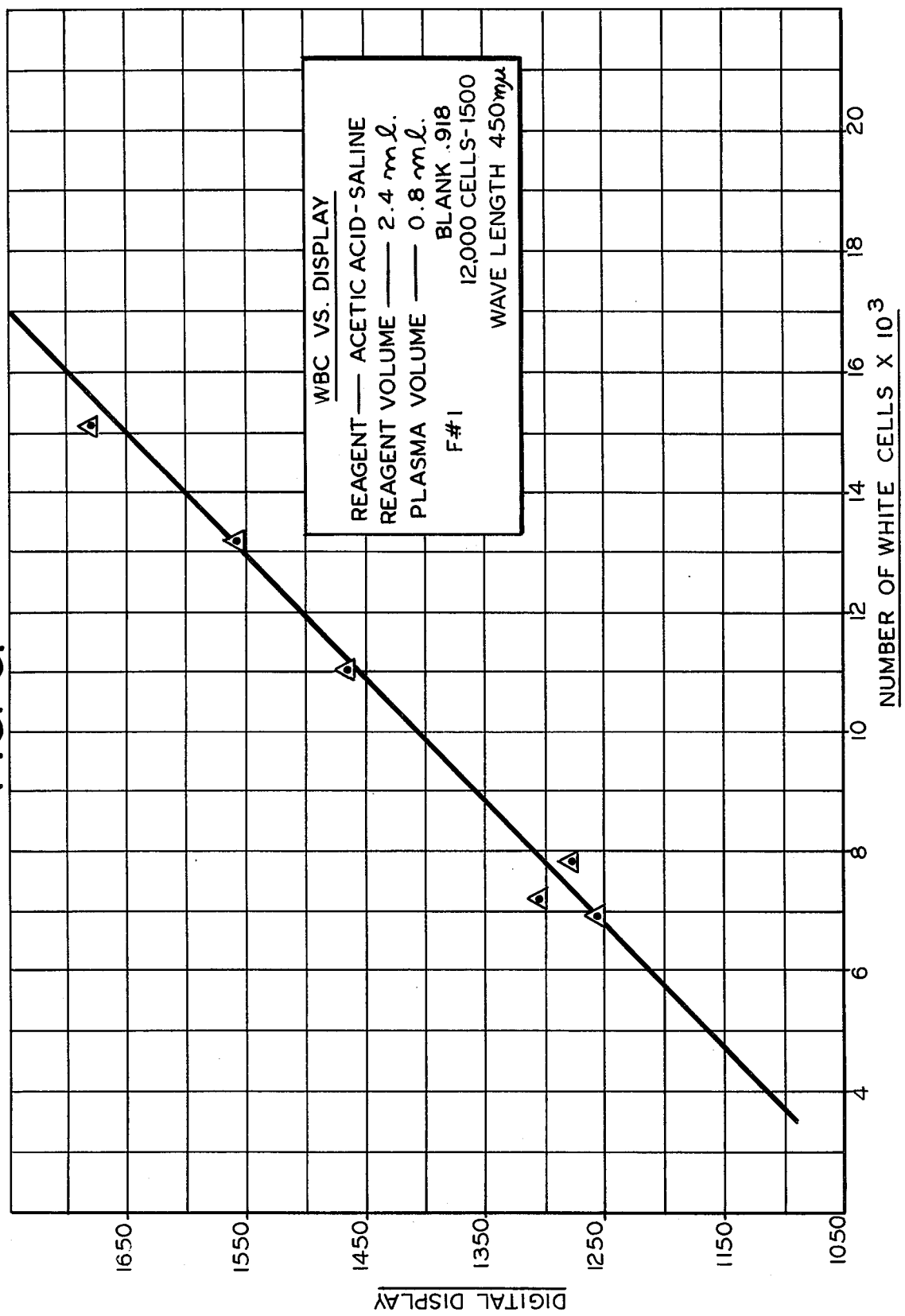

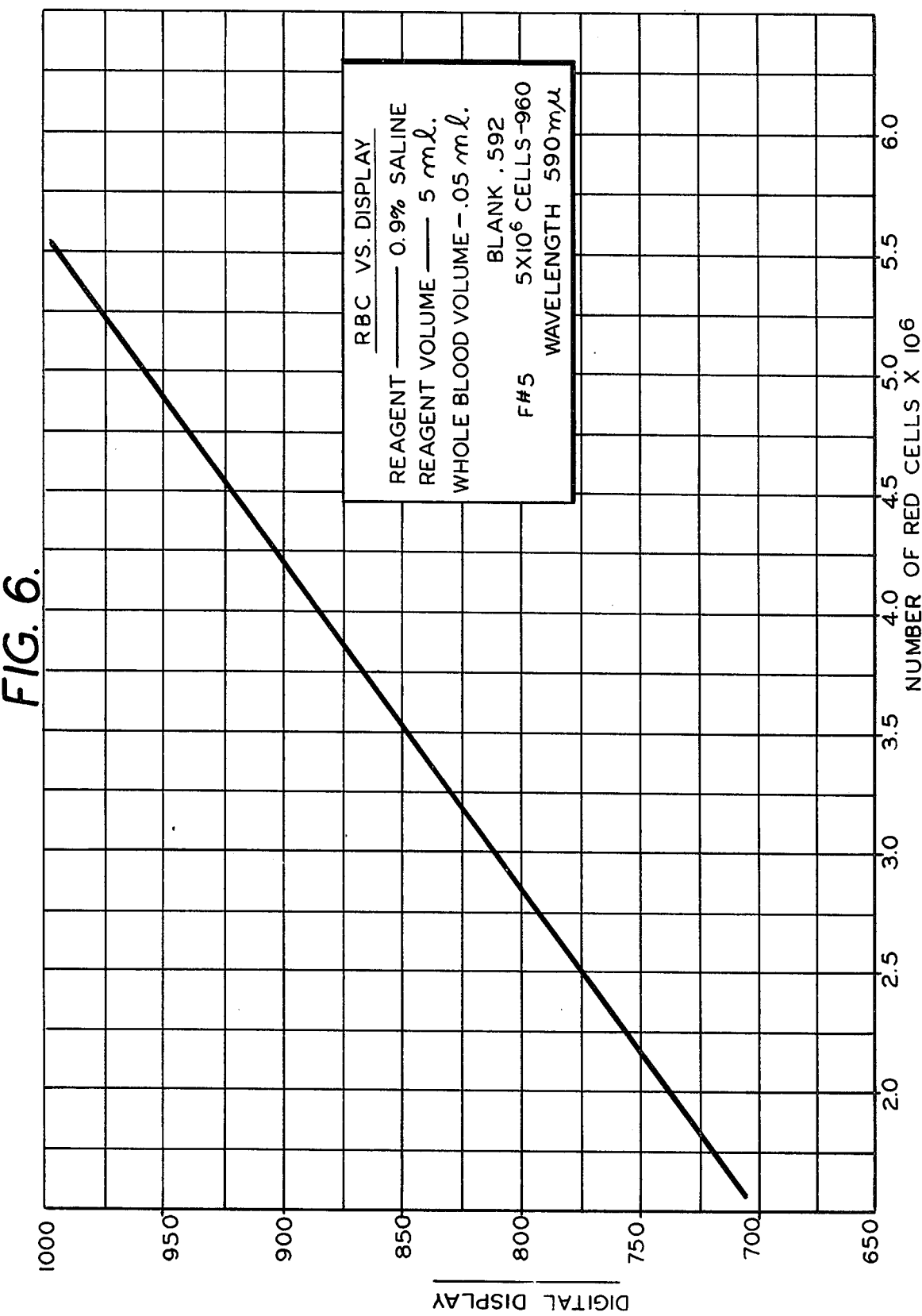

METHOD OF SIMULTANEOUSLY COUNTING BLOOD CELLS

This is a continuation of application Ser. No. 321,755, filed Jan. 8, 1973, now abandoned.

BACKGROUND OF THE INVENTION

1. Field of the Invention

The present invention relates to a method and apparatus for analyzing the quantity of a chemical substance as well as for enumerating the quantity of blood cells present in a predetermined blood volume.

2. Description of the Prior Art

Prior art blood cell counting methods and apparatus utilized in accomplishing such methods primarily all require movement of a blood sample through a constricted passageway in what is commonly termed the electrolyte counting method or by utilizing the detection and measurement of blood cell count at a scattering angle. One such constricted passageway blood cell counting procedure is disclosed in U.S. Pat. No. 2,656,508 wherein a diluted specimen of particles suspended in a fluid flows past a constricted current passage through which a current is passing. The flow of fluid through the constricted area changes the conductivity of that area and causes the individual particles to modulate the current, passing through the electrodes in a sequential detectable manner, the cells being counted one at a time. Similarly, U.S. Pat. Nos. 3,549,994; 3,657,725; 3,654,439 and 3,412,254 are exemplary of prior art blood cell counting devices which count the particles or cells by means of light interruption by the particle in a constricted passageway for advancing a counter one-by-one. Another such prior art device is disclosed in U.S. Pat. No. 2,875,666 wherein both red and white blood cells are counted simultaneously. However, in this instance, the red and white blood cells are stained and are then passed through a constricted passageway one-by-one so as to be sequentially counted in this fashion by means of subjecting the constricted passageway to a colored light source which comprises both the color to be absorbed by the cells being detected and the color to be transmitted. This light is filtered with a filter having a wavelength which corresponds to the light being absorbed by the cells being detected and the decrease in intensity of the light passing through the filter actuates a photocell which corresponds to the amount of cells passing through the constricted passageway in substantially successive or sequential fashion. However, these prior art devices are time consuming due to the quantity of time required to count the cells in successive or sequential fashion as opposed to being able to detect the overall quantity of blood cells in a given blood sample simultaneously with one measurement rather than a plurality of successive measurements. This time factor becomes particularly critical when a large number of samples are being tested such as in a hospital environment or a clinical testing laboratory. Furthermore, special types of tubes having such a constricted passageway of specified dimensions must be constructed and these special tubes increase the cost of the instrumentation.

In addition, prior art counting methods have not proved satisfactory with respect to the counting of leucocytes in that considerable effort must be expended so as to ensure that the leucocyte count is obtained substantially free of erythrocytes and other chemical constituents of the blood. Furthermore, users of such analyzers or blood cell counting instrumentation are normally also interested in determining the quantity of various chemical constituents, such as bilirubin, cholesterol, urea nitrogen, protein, glucose, cyanmethemoglobin, etc., of the blood, such as of the individual whose blood cell count is being determined. This is particularly so when such blood analysis is performed by a clinical testing laboratory or a hospital doing a complete blood test on a patient. Prior art methods and devices require the use of a separate chemical analyzer for determining the quantity of such chemical constituents in the blood, the requirement of an additional device in addition to the blood cell counting analyzer substantially increasing the cost of such instrumentation as well as being inefficient. Such chemical analyzer instrumentation may be of the type utilizing a colorimeter which produces an analog signal from the output of a photoelectric device, the amplitude of which signal is representative of a particular chemical substance sensed by a light filter. Such devices, however, to date have not been utilized in blood cell count analysis so as to provide a single instrument capable of providing both a blood cell count as well as an analysis of the chemical constituency of a blood sample. These disadvantages of the prior art are overcome by the present invention.

SUMMARY OF THE INVENTION

Analytical method and apparatus is provided wherein the quantity of blood cells suspended in a predetermined quantity of fluid comprising a blood fraction may be simultaneously counted as well as an analysis of a particular chemical constituent of a given blood sample may be performed in a single instrument utilizing filter photometry. The quantity of the particular chemical or the overall quantity of either red or white blood cells in a given blood sample is determined by preferably generating an analog signal whose amplitude is representative of either the quantity of the particular chemical or the overall quantity of the red or white blood cells, respectively, in a given blood sample. This analog signal is preferably converted to a digital signal and displayed by a readout device, this digital display being representative of the optical density of the light transmitted by a specified filter correlated to the specific cell count or chemical constituents being measured, this reading being linearly related to the blood cell count or quantity of chemical substance in the sample being tested.

When the apparatus is utilized for simultaneously counting the quantity of blood cells suspended in a predetermined quantity of fluid comprising a blood fraction, the apparatus preferably comprises a source of white light, a cuvette containing the suspended blood cells to be counted, the cuvette being adjacent to the light source so as to have the fluid initially illuminated thereby along an optical axis from the light source so as to illuminate substantially all of the suspended cells simultaneously, a light filter having an optical wavelength selected to substantially minimize any interference from any spurious chemical substances contained within the blood fraction due to absorption of the initial light by the spurious substances while passing light of the selected optical wavelength which has not been absorbed by the blood cells, the filter being aligned with the light source and the cuvette substantially in a direct line along the optical axis so as to intercept only light transmitted directly through the cuvette, a photodetector means for detecting the passed light and producing an output signal in response to the quantity of the directly transmitted light passed by the filter, the passed light being the quantity of light remaining after substantially all the absorption and scattering of the initial illumination by all of the suspended blood cells has occurred, and means for providing a count indication of the overall quantity of blood cells in response to the signal, the count indication being directly proportional to the quantity of the light passed by the filter, the blood cell count indication provided being linearly related to the optical density of the detected light. When erythrocytes are being counted, the wavelength of the filter is preferably in the visible spectrum outside of the absorption bands for hemoglobin, such as 5900 angstroms. When leucocytes are being counted, the blood fraction is substantially free of erythrocytes and the filter has a wavelength such as approximately 4500 angstroms. If desired, gentian violet may be utilized to stain the leucocytes so as to minimize the effects of body chemistry and the filter in such an instance may have a wavelength of approximately 6100 angstroms.

In preparing the sample for the enumeration of erythrocytes, the fluid utilized preferably comprises a mixed one to 100 and one dilution of whole blood in physiological saline. When it is leucocytes that are being enumerat the fluid preferably comprises a mixed one to four dilution of a final sediment containing the leucocytes in physiological saline, the final sediment resulting from the lower layer of the centrifuged one to four dilution of an initial sediment in acetic acid in physiological saline which is a lysing reagent for erythrocytes and any platelets present, the initial sediment resulting from the lower layer of a centrifuged one to four dilution of siphoned plasma in physiological saline, the siphoned plasma resulting from the uppermost layer of a separated mixed solution of whole blood and high molecular weight polysaccharide in physiological saline in a calibrated separation tube.

In performing the chemical analysis of a blood sample, the filter is changed so as to provide an appropriate filter correlated to the particular chemical substance whose quantity is being detected and, if desired, the readout scale may be changed, the cuvette containing the sample to be chemically analyzed merely replacing, in the instrument a cuvette containing blood cells whose overall quantity was to be counted the balance of the instrumentation being preferably identical to that utilized for determining a blood cell count.

BRIEF DESCRIPTION OF DRAWING

FIG. 5 is a graphic illustration of the leucocyte count versus optical density in accordance with the preferred method of the present invention;

FIG. 6 is a graphic illustration similar to FIG. 5 of the erythrocyte count versus optical density in accordance with the preferred method of the present invention.

DETAILED DESCRIPTION OF THE PREFERRED EMBODIMENT

Figure 1:
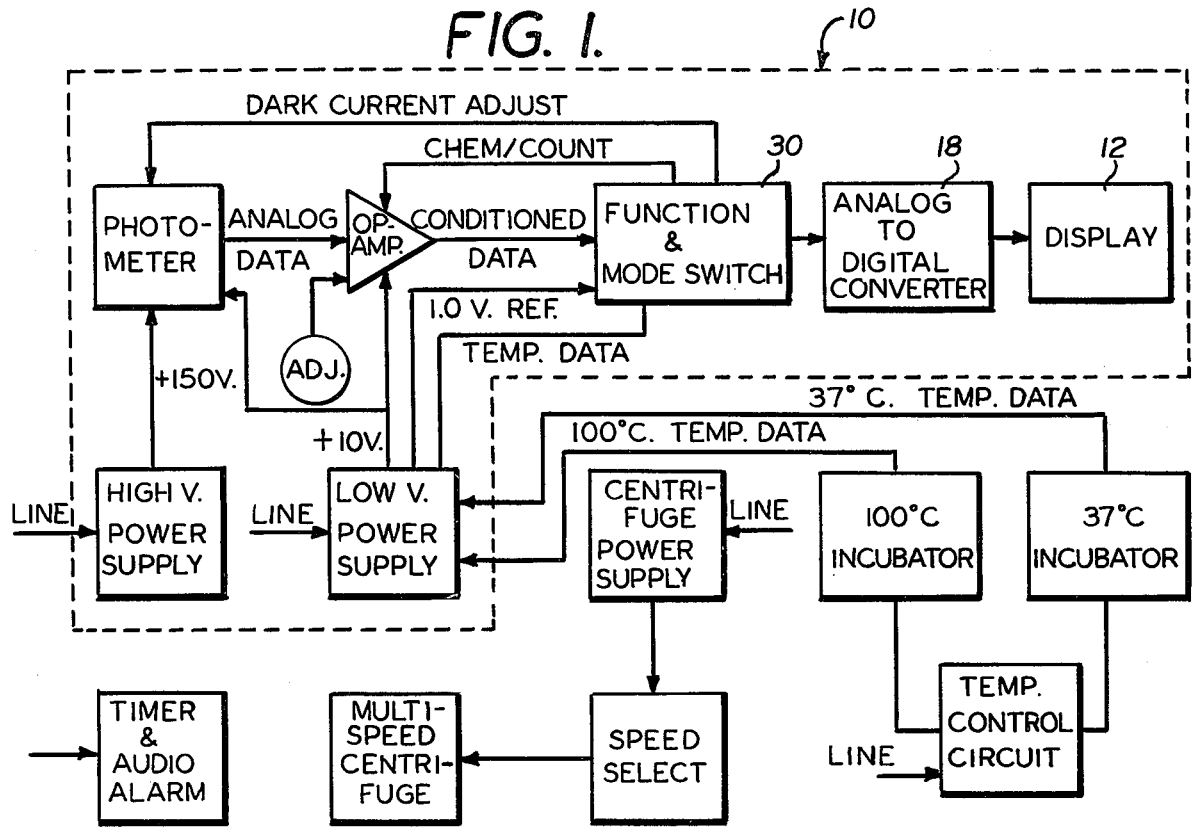
FIG. 1 is a block diagram of the preferred embodiment of the analytical apparatus of the present invention.
Figure 3:
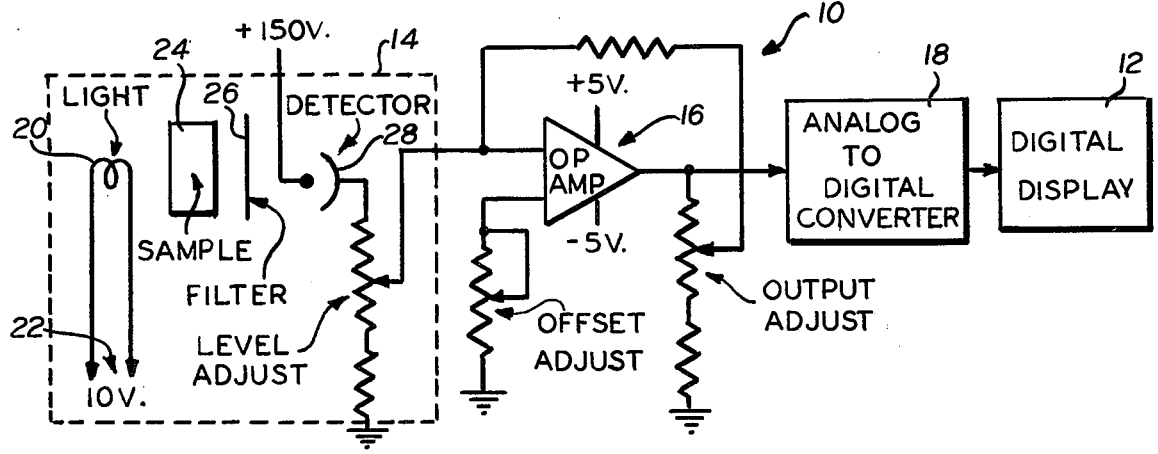
FIG. 3 is a block diagram partially in schematic of the preferred filter photometer analytical apparatus of the present invention.
Figure 4:
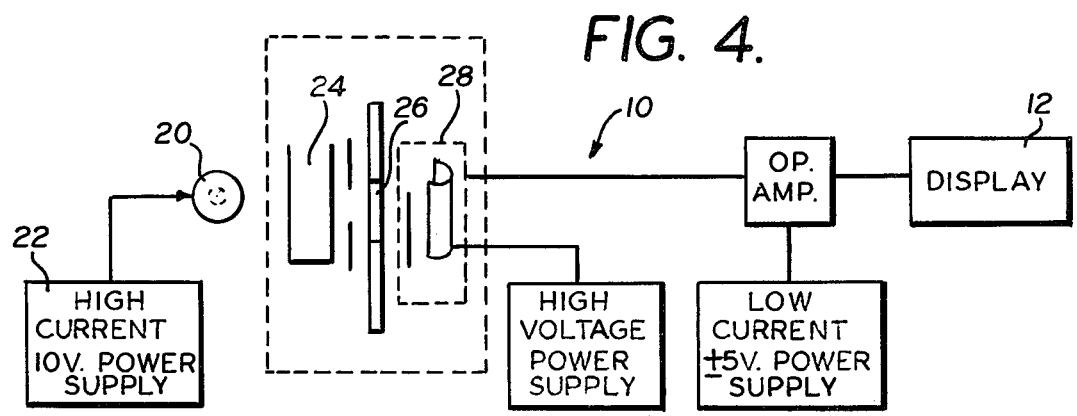
FIG. 4 is a diagrammatic illustration partially in block of the preferred filter photometer analytical apparatus of the present invention.

Referring now to the drawings in detail and initially to FIGS. 1, 3 and 4, the preferred analytical apparatus of the present invention shall be described and, thereafter, a preferred analytical method of the present invention both for enumerating leucocytes and erythrocytes as well as for detecting the quantity of a chemical substance present in a blood sample shall be described. As will be described in greater detail hereinafter, depending on the optical filter selected and the scale chosen to relate optical density measured or displayed to the quantity of erythrocytes or leucocytes present or the quantity of a given chemical substance present in a blood sample, the same instrumentation is preferably utilized for generating an analog signal whose amplitude is representative of the quantity of the given chemical substance present in the blood sample or the number of erythrocytes or leucocytes present in a given blood sample, this preferably being converted to a digital signal and displayed as a digital readout of percent transmission on a conventional digital display device 12, although if desired an analog type display may be provided without departing from the present invention.

In one mode of operation, the instrument is utilized as a colorimeter to measure the quantity of a given chemical substance in a blood sample which is being tested. The apparatus 10 preferably comprises a filter photometer portion 14 for generating an analog signal whose amplitude is representative of the quantity of the given chemical constituent of the blood sample being tested, this signal corresponding to an optical density value which is, as will be described in greater detail hereinafter, correlated to the quantity of the chemical constituent of the blood sample being tested, the optical density preferably being linearly related to such quantity. This analog signal is preferably fed to a conventional amplifier 16 which preferably conditions the input data in conventional fashion, such as by scale changing. The output signal of this operational amplifier 16 is preferably fed to a conventional analog to digital converter 18, such as the type manufactured by Digital Electronics, Hybrid Systems Corportion, or Texas Instruments. This digital signal output of converter 18 is then fed to the conventional digital display 12 whose readout is the value of optical density equivalent to the quantity of the given chemical constituent of the blood sample being tested. The operational amplifier 16 provides the proper linear relationship between optical density and a quantity of the chemical constituent in the blood sample being tested in conventional fashion in accordance with a predetermined linear functional relationship therebetween.

The digital display 12, by way of example, may include a conventional nixie tube arrangement and conventional activating circuitry therefor. As was previously mentioned, when the device is utilized for enumerating the quantity of leucocytes or erythrocytes present in a given blood sample, the circuitry is preferably identical with that previously described with the exception that the scale associated with the operational amplifier 16 which provides the functional linear relationship between the optical density and the quantity of the chemical constituency of the blood sample is changed so as to reflect the preferred linear relationship between the optical density and the quantity of erythrocytes or leucocytes in the blood sample being tested. In addition, as will be described in greater detail hereinafter, the particular filter associated with the filter photometer 14 protion of the instrument is changed in accordance with the test being performed.

Referring now to FIGS. 3 and 4, a specific means for generating the analog signal resulting from the blood to operational amplifier 16 is shown. A conventional source of light, which is preferably noncoherent white light 20, such as a conventional 10 or 15 watt lamp which is connected across a conventional regulated power supply 22, for illuminating the sample to be tested is provided. Conventional means are provided for placing a conventional vial or cuvette 24 containing the material to be tested, whether a fluid comprising a blood fraction containing erythrocytes or leucocytes to be counted or containing a chemical constituent of the blood sample whose quantity is to be detected, adjacent to the light source 20 and aligned therewith along an optical axis from the light source of the light emitted therefrom so as to illuminate substantially all the suspended cells simultaneously within the fluid comprising the blood fraction if that is the test being performed or to illuminate substantially the entire sample being tested for chemical constituency if that is the test being performed.

A conventional light filter 26 having an optical wavelength of a selected value so as to pass light of the selected optical wavelength which has not been absorbed by the erythrocytes or leucocytes being counted if that is the test being performed or a wavelength which will pass unabsorbed light if the constituent to be detected is present in the curvette 24 if that is the test being performed, is preferably located along the optical axis between the cuvette 24 in a conventional photo detector tube 28, aligned with the light source 20 and the cuvette 24 so as to preferably intercept only light transmitted directly through the cuvette 24. The photo detector 28 is preferably a conventional photo detector tube having a response range throughout the visible light spectrum, the photo detector 28 detecting the light passed by filter 26 and producing an analog output signal in response to the quantity of the directly transmitted light passed by the filter 26.

As will be described in greater detail hereinafter, in the instance when the erythrocytes or leucocytes are being counted, this passed light represents the quantity of light remaining after substantially all the absorption and scattering of the initial illumination from source 20 by all of the suspended erythrocytes or leucocytes present in the cuvette 24 has occurred. This photo detector 28, as shown in FIG. 3, has its anode electrically connected, preferably, to a conventional regulated high voltage power supply and its cathode connected to the input to operational amplifier 16, the photo detector 28 having a spectral response which preferably peaks in the mid visible spectrum. When the instrument is utilized to detect the quantity of a given chemical constituent of a blood sample present in cuvette 24, the data output display is preferably a measurement of percent transmission of the substance whereas when the instrument is utilized in the cell counting mode, a conventional function and mode switch 30 (FIG. 1) associated with the digital display is utilized to switch the display scale of the digital display so that the data output is a relative display of the amount of light transmitted.

The preferred linear relationship between the optical density output displayed by digital display 12 and the erythrocyte or leucocyte count in accordance with the preferred method of the present invention is illustrated in FIGS. 5 and 6 and will be described in greater detail hereinafter with reference to the preferred method of the present invention.

Figure 7:
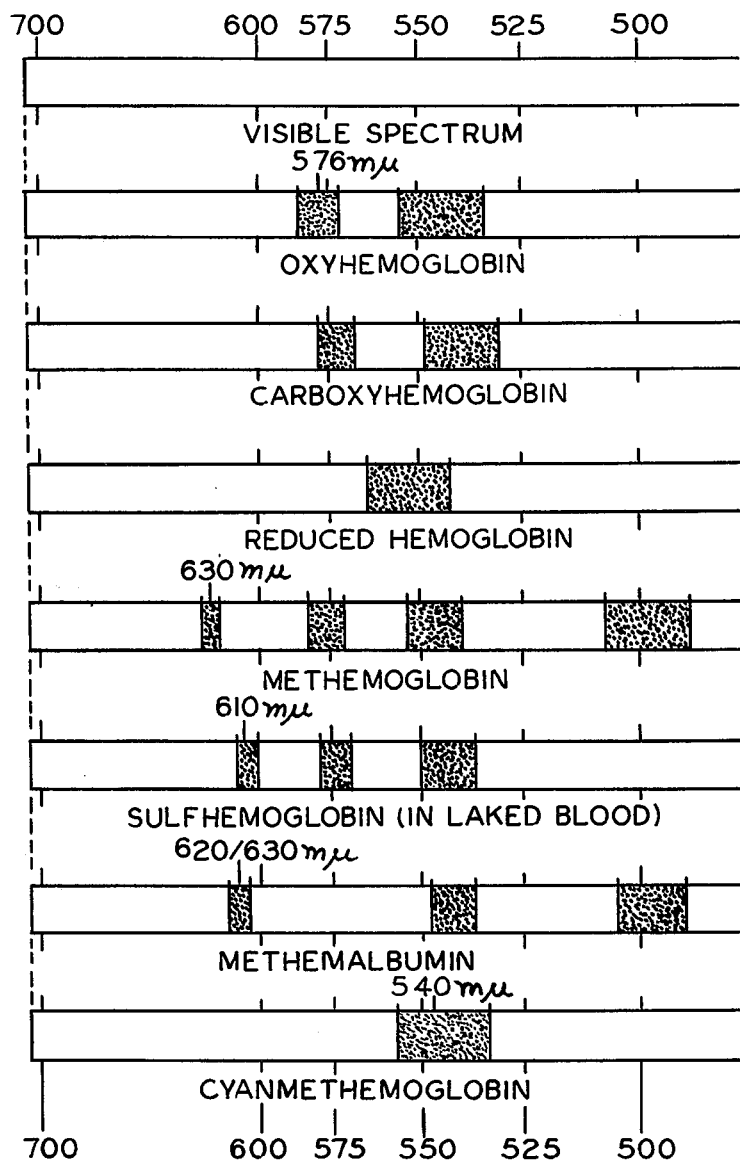
FIG. 7 is a graphic illustration of the absorption bands of hemoglobin in the visible light spectrum.

In discussing the preferred method of the present invention, the method of enumerating the erythrocytes or leucocytes present in a given blood sample shall be described, with the method for enumerating erythrocytes being described first. Prior to testing a given blood sample in order to determine the count of the quantity of erythrocytes present in a given blood sample, the test fluid which comprises a blood fraction having the erythrocytes to be counted suspended therein must preferably be prepared. In order to prepare this test fluid, preferably a 1:101 dilution of whole blood in a reagent such as preferably physiological saline is prepared, such as by mixing the cuvette containing this diluted solution several times such as by inversion. The cuvette 24 preferably contains whatever given volume is desired for purposes of the test so as to provide a standard for the test, the quantity of erythrocytes preferably being provided in million cells per cubic millimeter. Most preferably, the reagent volume comprises five milliliters of 0.9 percent physiological saline for a whole blood volume of 0.05 milliliters. The instrument is preferably calibrated for the use of a standard blank which provides an optical density of 0.592 for purposes of the preferred method of the present invention in accordance with the graph illustrated in FIG. 6. This optical density is provided by utilizing a filter 26 whose optical wavelength is preferably 5900 angstroms which value enables a linear relationship between the quantity of erythrocytes and the measured optical density. This wavelength is preferably selected to substantially minimize any interference from any spurious chemical substances contained within the blood fraction due to absorption of the initial illumination impinging on the sample contained in the cuvette 24 by such spurious substances while passing light of the selected optical wavelength which has not been absorbed by the erythrocytes contained within the test fluid. For purposes of enumerating the quantity of erythrocytes present in the test fluid, the selected optical wavelength is preferably outside the absorption bands for hemoglobin which absorption bands are illustrated in FIG. 7 for oxyhemoglobin, carboxyhemoglobin, reduced hemoglobin, methemogolobin, sulfhemoglobin, methemalbumin and cyanmethemoglobin. As previously mentioned, most preferably the wavelength chosen is 5900 angstroms although other values may be chosen without departing from the present invention. By way of example, the filter 24 utilized in providing the linear relationship illustrated in FIG. 6 is 5900 angstroms.

As was previously mentioned, only the light directly transmitted through the cuvette 24 is intercepted by the filter 26, the light passed by the filter preferably being the quantity of light remaining after substantially all the absorption and scattering of the initial illumination by all of the suspended erythrocytes has occurred and representing the quantity of this light which has not been absorbed by the erythrocytes. The proper scale for the operational amplifier 16 is selected prior to beginning the test so as to provide the functional relationship illustrated in FIG. 6. Thereafter, the cuvette 24 containing the prepared test fluid sample is placed in the cuvette well adjacent the light source 20 and the optical density displayed on digital display 12 is read and compared with the graphic illustration in FIG. 6 so as to determine the corresponding erythrocyte count per cubic millimeter.

By way of example, the following table of values defines the preferred linear relationship between erythrocyte count and optical density, as displayed on digital display 12, illustrated in FIG. 6, assuming the preferred reagent volume, whole blood volume, reagent concentration and blank value of optical density discussed above, typical values being as follows:

| Optical Density X 1000 | No. of Erythrocytes X 1 Million |
|---|---|
| 700 | 1.48 |
| 720 | 1.75 |
| 750 | 2.17 |
| 780 | 2.58 |
| 800 | 2.85 |
| 820 | 3.13 |
| 850 | 3.54 |
| 880 | 3.95 |
| 900 | 4.22 |
| 920 | 4.50 |
| 950 | 4.91 |
| 980 | 5.32 |
| 1000 | 5.59 |
| 1020 | 5.87 |
| 1080 | 6.69 |
| 1100 | 6.97 |

Thus, in accordance with the preferred method of the present invention, the entire or overall quantity of erythrocytes contained within the test fluid may be counted simultaneously by virtue of a single measurement.

Figure 2:
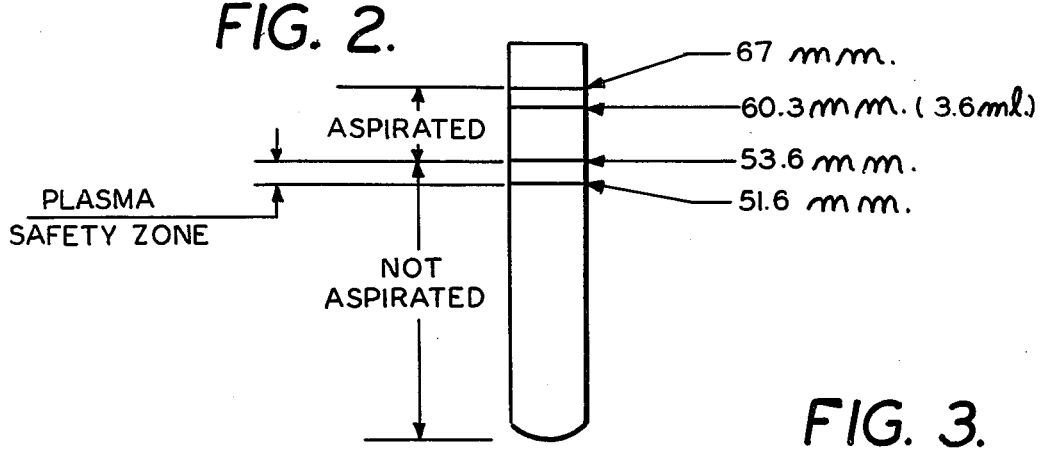
FIG. 2 is a diagrammatic illustration of a separation tube utilized in practicing the preferred method of the present invention.

Similarly, in order to count the number of leucocytes present in a given blood volume, the test fluid must preferably be prepared prior to performing the enumeration thereon, there normally being approximately 500 erythrocytes for every leucocyte in human peripheral blood. In order to accomplish this leucocyte separation, a calibrated separation tube, such as illustrated in FIG. 2, is preferably utilized. Preferably, the whole blood is added to the tube up to a 3.6 milliliter mark. High molecular weight polysaccharide in physiological saline is added up to the 4.0 milliliter mark on the calibrated separation tube. The contents of the tube are then preferably mixed, such as by inverting the tube approximately 12 times and the tube is then placed in an upright position. The erythrocyte layer is then allowed to reach the 51.6 millimeter mark of the tube and the plasma from the 53.6 millimeter to the 67 millimeter mark of the tube is then preferably siphoned off, this plasma volume being approximately 0.8 milliliters. Preferably, these points for the separation tube are chosen so as to obtain a constant volume of plasma, give a relative linearity to the leucocytes, maintain a relatively high plasma concentration in situations of high hematocrit for erythrocyte numbers and to give a quantity of plasma necessary for a 1:4 dilution. Preferably, the tube is free from all defects and constructed of a material that has limited or no effect on the action of the settling of the erythrocytes or leucocytes and whose inside surface is free from any physical defects which would impede or vary the rate of settling.

The resultant siphoned plasma is then preferably diluted 1:4 in physiological saline in a cuvette. The contents of this cuvette are preferably mixed such as by inverting several times and the cuvette is then preferably centrifuged for five minutes at 1000 rpm. The centrifuged cuvette is then removed from the centrifuge. Most preferably, the contents of the cuvette are centrifuged so as to provide a bottom layer in the cuvette containing the formed elements minus platelets and a top layer containing a solution of plasma protein, physiological saline, platelets and chemical constitutents normally found in plasma. The top layer is then removed and discarded, being careful not to disturb the lower layer. Preferably, a reagent capable of lysing any residual erythrocytes and/or platelets is then added to the remaining sediment to maintain the original 1:4 dilution. Most preferably, this reagent is a solution of acetic acid in physiological saline. The cuvette and its contents are then preferably mixed and centrifuged once again so as to form two layers as previously mentioned. Most preferably, the cuvette is centrifuged once again for five minutes at 1000 rpm. The upper layer is once again removed and discarded. Then, preferably, physiological saline in an amount necessary to maintain a 1:4 dilution is added to the remaining sediment to provide the test fluid for the leucocyte enumeration. As with the erthrocyte enumeration, the filter 26 is selected having an optical wavelength selected to substantially minimize ay interference from any spurious chemical substances contained within the resultant blood fraction due to an absorption of the initial light illuminating the cuvette by the spurious substances while passing light of the selected optical wavelength which has not been absorbed by the leucocytes.

Most preferably, for purposes of the preferred leucocyte enumeration a filter having an optical wavelength of 4500 angstroms is selected to provide the preferred linear relationship between the number of leucocytes present and the corresponding optical density as graphically illustrated in FIG. 5. The scale associated with the operational amplifier 16 is preferably selected so as to provide this preferred linear relationship and the cuvette 24 containing the prepared test fluid for the leucocyte count is inserted into the cuvette well and the appropriate optical density corresponding to the number of leucocytes present in the test fluid is displayed on digital display 12. The number of leucocytes may then be gotten by referring to the graphic illustration in FIG. 5 by comparing the optical density reading against the corresponding number of leucocytes. By way of example, the following table of typical values defines the preferred linear relationship between leucocyte count and optical density, as displayed on digital display 12, illustrated in FIG. 5, assuming a preferred reagent volume of 2.4 milliliters, a preferred plasma volume of 0.8 milliliters, a preferred reagent of acetic acid in physiological saline, a preferred optical density value of 0.918 for a blank and a preferred optical wavelength of 4500 angstroms for the filter, 12,000 leucocytes corresponding to an optical density of 1.5, are as follows:

| Optical Density X 1000 | No. of Leucocytes X 1000 |
|---|---|
| 1100 | 3.744 |
| 1150 | 4.770 |
| 1200 | 5.795 |
| 1250 | 6.821 |

-continued

| Optical Density X 1000 | No. of Leucocytes X 1000 |
|---|---|
| 1300 | 7.847 |
| 1350 | 8.872 |
| 1400 | 9.898 |
| 1450 | 10.924 |
| 1500 | 11.949 |
| 1550 | 12.975 |
| 1600 | 14.000 |
| 1650 | 15.026 |
| 1700 | 16.052 |
| 1750 | 17.077 |

Thus, utilizing the preferred method of the present invention for enumerating leucocytes, the entire overall quantity of leucocytes in a given volume of blood can be simultaneously obtained by a single measurement, the quantity of leucocytes above being preferably provided in terms of thousands per cubic millimeter.

As was previously mentioned, when utilizing the preferred analytical apparatus of the present invention to determine the quantity of a particular chemical constituent present in a given blood volume, the instrument is preferably utilized as a filter colorimeter and the data output display is a measurement of percent transmission of the substance which is preferably calibrated in a linear relationship between the optical density displayed, the optical density being equivalent to the logarithm of the ratio for the intensity of the attenuated beam after it passes through the solution to the intensity of the original beam, and the quantity, preferably in milligrams per liter, of the chemical constituent of the blood being tested. By way of example, if bilirubin is the substance being tested, and the optical wavelength of 5200 angstroms is preferably utilized for the filter with a reagent such as methanol-$H_2O$-diazo, the linear relationship is defined by a line connecting the points 0.5 milligrams, 0.0458 optical density; 2.0 milligrams, 0.1487 optical density and 5.0 milligrams, 0.347 optical density.

In practicing the preferred method of the present invention, with respect to determining the chemical content of a blood sample, an optical wavelength is selected for the filter corresponding to the substance being tested for so as to pass light if the substance to be detected is present in the cuvette, light of the selected wavelength being absorbed by the substance present in the cuvette. Any desired constituent of blood can be tested and quantized by use of the present device such as cholesterol, glucose, urea nitrogen, serum glutamic, oxyalacetic transaminase, protein, serum glutamic pyruvric transaminase and cyanmethemoglobin, depending on the selection of the appropriate filter 24 and the appropriate reagent for the chemical substance being detected the reagents being well known for these colorimetric determinations and a linear relationship between optical density and quantity of chemical substance present preferably being provided. The wavelength of 6100 angstroms being preferably utilized for testing for cholesterol and glucose, a wavelength of 4500 angstroms being preferably utilized when testing for urea nitrogen, and a wavelength of 5200 angstroms being preferably utilized when testing for bilirubin, cyanmethemoglobin, protein, serum glutamic pyruvric transaminase and serum glutamic oxyalacetic transaminase, by way of example.

If desired, in performing the enumeration of leucocytes, the leucocytes can preferably be stained with gentian violet in which instance a selected optical wavelength of 6100 angstroms is preferably utilized for the filter 26 in performing the leucocyte enumeration, minimal interference from body chemistry being provided at this wavelength and, thus, the leucocytes need not be preferably treated to eliminate such body chemistry interference.

Thus, by utilizing the analytical apparatus and preferred method of the present invention, both blood cell enumeration and chemical analysis of a blood sample may be performed by a single instrument and such blood cell enumeration may be obtained by a single measurement.

It is to be understood that the above described embodiments of the invention are merely illustrative of the principles thereof and that numerous modifications and embodiments of the invention may be derived within the spirit and scope thereof.

What is claimed is:

1. An analytical method for counting the quantity of blood cells suspended in a predetermined quantity of fluid comprising a blood fraction comprising the steps of preparing said fluid for simultaneously counting the overall quantity of leucocytes suspended in said fluid, said preparing step comprising the steps of delivering a predetermined volume of whole blood to a calibrated separation tube, adding a predetermined volume of high molecular weight polysaccharide in physiological saline, mixing said whole blood and said polysaccharide-physiological saline volumes and letting said mixture stand to form an erythrocyte layer and a plasma layer above said erythrocyte layer, waiting until said layer of erythrocytes reaches a predetermined volume level in said tube and siphoning off said plasma layer to provide a predetermined volume of plasma, said siphoned plasma being an intermediary preparation, suspending said siphoned plasma in a reagent capable of lysing any residual erythrocytes and platelets to form a dilute final sediment, illuminating said dilute final sediment with a white light along an optical axis so as to illuminate substantially all of said suspended leucocytes substantially simultaneously; filtering the light directly transmitted through said dilute final sediment at an optical wavelength which passes light which has not been absorbed by said leucocytes, and providing a simultaneous count indication of said overall quantity in response to said filtered light.

2. An analytical method in accordance with claim 1 wherein said lysing reagent comprises acetic acid in physiological saline.

3. An analytical method in accordance with claim 1 wherein said filtering step comprises filtering said directly transmitted light substantially at an optical wavelength of 4500 angstroms.

4. An analytical method in accordance with claim 1 wherein said preparing step further comprises staining said suspended leucocytes in said dilute final sediment with gentian violet and said filtering step comprises filtering said directly transmitted light substantially at an optical wavelength of 6100 angstroms.

5. An analytical method in accordance with claim 1 wherein said count indication providing step comprises providing an overall leucocyte count which is linearly related to the optical density of said filtered light.

* * * * *